United States Patent [19]

Keates et al.

[11] Patent Number: 4,799,785
[45] Date of Patent: Jan. 24, 1989

[54] CORNEA CONTOUR MAPPING

[76] Inventors: Richard H. Keates, 264 N. Drexel Ave., Columbus, Ohio 43209; Richard T. Schneider, 3550 N.W. 33rd Pl., Gainesville, Fla. 32605

[21] Appl. No.: 920,049

[22] Filed: Oct. 17, 1986

[51] Int. Cl.$^4$ ............................. A61B 3/10; A61B 5/10
[52] U.S. Cl. ..................................... 351/212; 128/774
[58] Field of Search .................. 351/212; 128/303.14, 128/303.18, 774; 33/511, 512, 552, 560; 356/356, 376, 393, 394

[56] References Cited

U.S. PATENT DOCUMENTS

| 4,444,204 | 4/1984 | Bryant et al. | 33/512 |
| 4,673,817 | 6/1987 | Oomen | 356/376 |

Primary Examiner—John K. Corbin
Assistant Examiner—Jay Ryan
Attorney, Agent, or Firm—Bert J. Lewen; Henry Sternberg

[57] ABSTRACT

An apparatus and method for mapping the cornea is described. The apparatus comprises a probe having a multiplicity of parallel pins bundled together which are reciprocally movable with respect to one another. The pins are maintained in parallel and slidable relationship with one another and, after the leading end of the pins is urged against the surface of the cornea so that the ends thereof form a surface mirroring the contour of the cornea, the pins may be locked together in fixed relationship. A detector is used to sense the relative position of the pins, the sensed positions are stored, and the stored values used to depict the contour of the cornea on a two-dimensional surface such as a display terminal or as hard copy on paper. A computer is used to obtain the data from the detecting means, to store the data, and, by means of an appropriate algorithm, to graphically generate the two-dimensional image. Most preferably, the pins are arranged in the form of straight radial lines forming concentric annular rings.

3 Claims, 6 Drawing Sheets

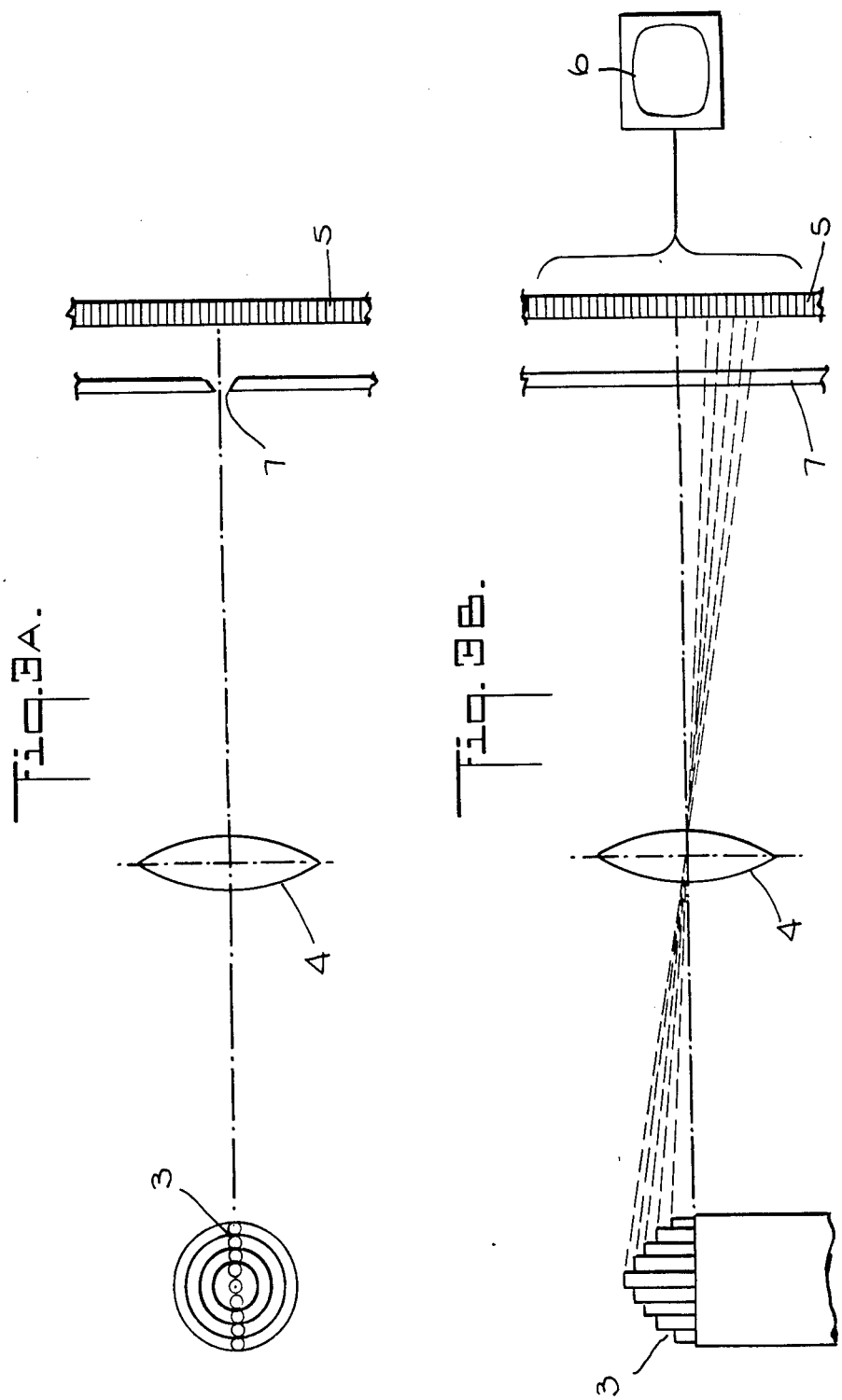

CORNEA CONTOUR MAPPING

BACKGROUND OF THE INVENTION

It has long been desired to measure the anterior surface of the cornea, initially for providing an objective measurement of the patient's anterior cornea astigmatism. Herman von Helmholtz, in the 19th Century, developed the first keratometer and other investigators improved this device to make the instruments that are in clinical use today. These early developments and the principles of operation of the keratometer are described in R. Mohrman, "The Keratometer," in T. D. Duane (ed.), *Clinical Ophthalmology*, Vol. 1, Chap. 60, pages 1–12.

In recent years, corneal contact measurement has become of increasing importance in connection with the fitting of contact lenses. In addition to the keratometer, the area of the cornea has been studied with the photokeratometer, stereophotogrammetry, autocollimation keratometers, contact lens and fluorescein methods, interferometry, holographic techniques, moire fringe topography, and profile methods. However, these apparatuses and techniques have not been entirely satisfactory. For example, J. J. Rowsey, *Topographical Analysis*, describes the deficiencies of these techniques and proposes the use of the photokeratoscope. Unfortunately, even this latter device has the disadvantages of inducing aberrations about the visual axis and requiring the talents of an experienced photographer. See J. J. Rowsey et al., *Arch. Ophthalmol.* 99, June 1981, p. 1093.

BRIEF DESCRIPTION OF THE INVENTION

In accordance with the instant invention, the deficiencies of the aforesaid devices are overcome by employing an apparatus and method which directly measures the corneal contour.

The apparatus used comprises the following:

1. A probe comprising a multitude of cylindrical pins bundled together and arranged, when viewed from the ends of the pins, substantially in the form of annular rings. In a first state, the pins are freely slidable with respect to one another. In a second state, the pins are locked into a fixed position with respect to one another. When used to measure the cornea, the forward end of the bundle of pins is positioned perpendicularly to the eye and each pin is gently urged against the cornea. When the end of each pin is in contact with the cornea surface, the pins are locked in position.

2. A detector or reader which serves to measure the relative position of each of the pins, preferably by observing the relative position of the pins at the back end of the probe, that is, the ends of the pins that are opposite those which are brought into contact with the cornea.

3. Memory means for storing the relative position of each of the pins.

4. Graphing means capable of reading the data stored in the memory means and for depicting graphically images corresponding to the contour of the cornea.

The physician operates the instrument as follows:

Initially, the probe is positioned vertically above a flat surface, the locking means released, and the pins allowed to fall upon the surface. When the forward ends of the pins form a flat surface, the locking means is engaged.

To measure the contour of the cornea, the patient assumes a supine position and the probe is held in close proximity or just touching the cornea. The friction brake is then disengaged, the pins allowed to drop down and hug the cornea, and, while the forward ends of the pins are still in contact with the cornea, the locking means is again engaged. Thereafter, the probe is inserted in the reader, wherein the detector senses the position of the back ends of the probe which, it will be understood, reflects the contour of the cornea.

BRIEF DESCRIPTION OF THE DRAWINGS

FIGS. 3a and 3b show a schematic view of the pins in the probe after the probe has been brought into contact with the patient's cornea, the detector, and a computer used to store the data from the reader and to graph the contour of the cornea.

FIG. 3a shows a view from above wherein the ends of the pins are shown and

FIG. 3b shows a side view wherein the side of the pins is shown in relationship to the detector array.

DETAILED DESCRIPTION OF THE INVENTION

The device of the instant invention is intended to map the surface of the cornea and display this map prospectively on the screen of a personal computer, said computer being programmed so as to permit the operator to rotate the display and look at the projection of the surface of the cornea from any desired angle. The device of the invention is capable of mapping the contour of the cornea and displaying it on, for example, a cathode ray tube, in only a matter of seconds.

Figure 1:
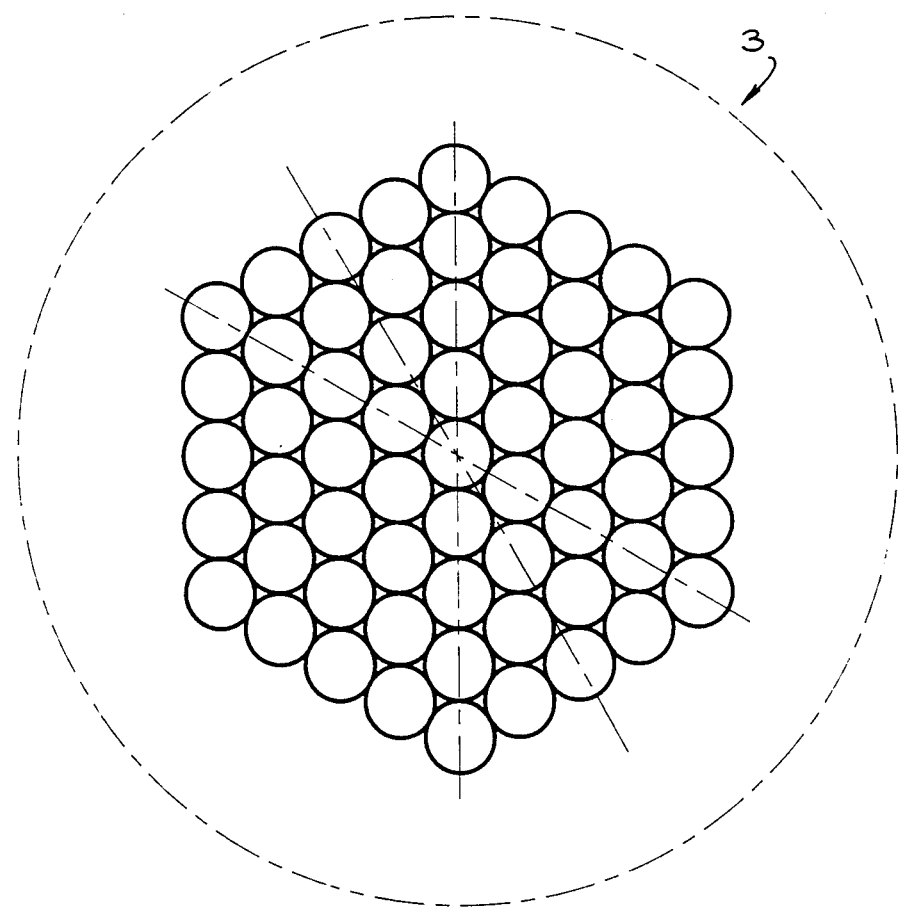
FIG. 1 illustrates an end view of a set of the cylindrical pins in the probe.

As set forth above, the device of the invention comprises a plurality of primary units: a probe, a reader, memory means, and graphing means for displaying the contour of the cornea. In the preferred embodiment of the invention, the probe consists of a bundle of equal length cylindrical pins which, when viewed from the end, form a series of annular rings. This configuration is depicted in FIG. 1. The diameter of each pin is desirably 0.010 in. (250 micrometers) and the spacing between the pins in the radial direction is 0.005 in. (125 micrometers). The number of substantially annular rings of the pins depends on the coverage of the cornea desirable. For example, for a 10 mm diameter coverage of the cornea, 13 rings would be required; 20 rings would cover an area of approximately 15 mm in diameter. The probe, including the sheathing is generally cylindrical in appearance, as shown in FIG. 2.

Figure 2A:
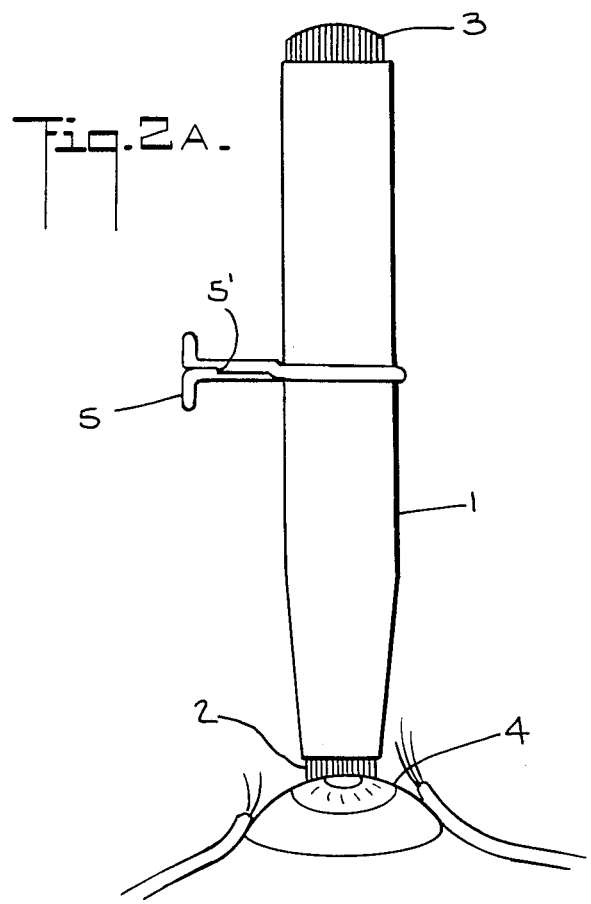
FIG. 2a shows a top view of the probe showing the pins projecting from the sheathing.
Figure 2B:
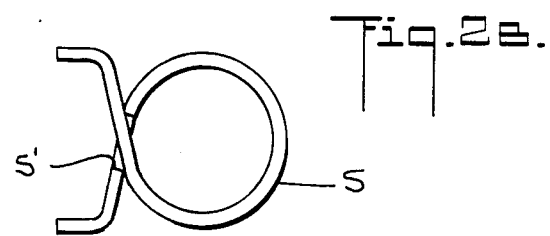
FIG. 2b illustrates a spring clip used to lock the cylindrical pins in the probe in a fixed position.

FIG. 2a represents a longitudinal view of the probe. The numeral 1 depicts the sheathing. Numeral 2 illustrates the forward ends of the bundle of pins which are brought into contact with the cornea 4, and numeral 3 shows the back ends of the pins, the contour of which ultimately corresponds to the contour of the cornea. The spring clip 5, the front view of which is shown in FIG. 2b, is used to hold the pins in a fixed position once the pins assume the contour of the cornea 4. The spring clip functions by spring action and may be released by pushing the ends together. A notch 5' is provided to hold the clip in the open position. The notch 5' is easily disengaged by a slight sidewise motion.

To ascertain the contour of the patient's cornea, the operator would position end 2 against the cornea surface after the eye has been properly anaesthetized. The forward end of each of the pins gently slides forward until it is in contact with the cornea surface. The pins slide easily with respect to each other and may be lubricated by any appropriate lubricant. Thereafter, the pins are locked into a fixed position by the spring clip. The back end 3 of the probe reflects the surface contour of the cornea.

Alternatively, the pins may be composed of a magnetic material which can be locked in position by the application of a magnetic field across the body of the pins. Naturally, the pins should lose their magnetism when the magnetic field ceases to be applied. If the pins retain their magnetism, a demagnetizer may be used between measurements.

After the pins in the probe are locked into position, the probe is transferred to the reader which measures the relative position of each of the pins projecting out of the back end of the probe 3. In order to facilitate the measurement of this relative position, alternate rings of the pins are marked in contrasting colors. For example, every other ring of pins may be black while the intermediate pins are white. In the reading process, the probe is positioned vertically that is, perpendicular to the principal axis of the lens 4, and rotated in steps. The number of steps is equal to the number of pins in the largest ring. At each step (rotational), the position of all pins in a vertical plane, from the outermost pin to the pin in the center of the probe, are read through the center of the lens 4 and the observation slit 7 (as shown in FIG. 3). The lens projects an image of the end of each pin onto the detector array 5 (126×256 detectors of 6.8 micrometers in size; reference: IS32A, Detector Array; Micron Technology, Inc.). The observation slit 7 is one pin in width. Assuming a 1:1 image is formed, then the 250 micrometer pin covers a slice on the detector array about 19 detectors wide and typically also about that high per pin, of course depending on how much the white or black end sticks out over its predecessor. The length of the exposed end of the pin is now determined by counting the number of pins in the upwards direction until a drastic change of intensity takes place (change from black to white or white to black). After one radial set of pins has been read, the device is mechanically rotated and the next radial set of pins is read.

After the relative positions of all of the radial sets of pins have been read and stored within the memory of the computer 6, the graphical display of the contour of the cornea may be illustrated on the cathode ray tube of the computer 6.

As to the computer routine, this is a straightforward procedure. The array is read sequentially in the vertical direction with a counter statement (n=n+1) and an "if" statement, which determines if an intensity change takes place. Since this will be done 19 times, the 19 results can be averaged into a more precise result. If the cornea were truly symmetrical, the pin arrangement would be the same as viewed in each rotational step and, therefore, reading one rotational slice would be sufficient. However, this is not the case. The probe must be rotated to the next slice (represented by the next pin of the largest ring) repeatedly and read again until the probe has fully rotated.

Data are stored in addresses corresponding to ring number (R) and pin number (P). Weight (W) is the information content stored in each address. W represents the number of vertical detectors in each slice between changes of intensity. This represents the length of the pin sticking out above its predecessor. The core map therefore represents a two-dimensional topographical map of the probe, whereby W is interpreted as an elevation. The perspective three-dimensional map is obtained by computing the length of a display vector starting at the center of a sphere and ending at the data point and then distorting the length and direction of the vector according to the laws of the particular perspective desired. The sphere chosen is an ideal normal cornea. The weight (W) of such a cornea can be calculated beforehand with commonly known spherical geometry formulas. Deviations between the measured weight and the ideal weight are translated into change of direction and length of the display vector by computing the appropriate spherical triangles. Changing the direction and length of the display vectors will distort the surface of the displayed sphere. Examples of such distortions are given in the attached FIGS. 4a–c.

A wide variety of computers may be used in conjunction with the instant invention. Most preferable is an inexpensive, readily available device such as an IBM-compatible personal computer.

While the invention can be adequately practiced using a standard monochrome monitor, a colored monitor can be advantageously employed. Such monitor could highlight the portion of the cornea's contour which deviates from the truly spherical, thereby simplifying the observation of irregularities on the cornea surface.

Figure 4A:
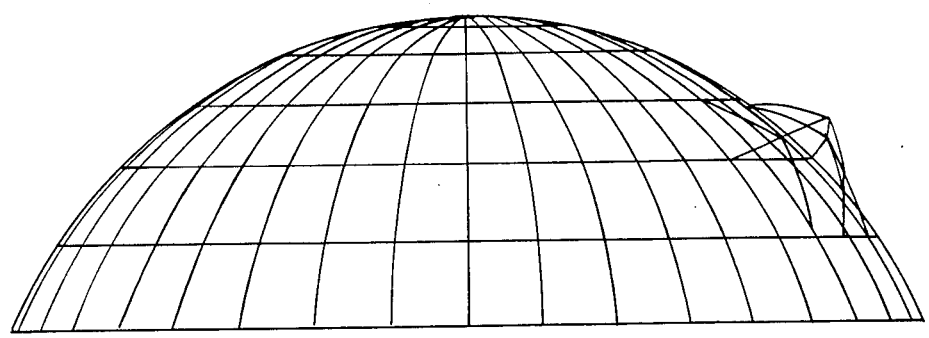
FIG. 4 illustrates a series of two-dimensional contour graphs showing the surface area of the cornea as viewed from different perspectives.
Figure 4B:
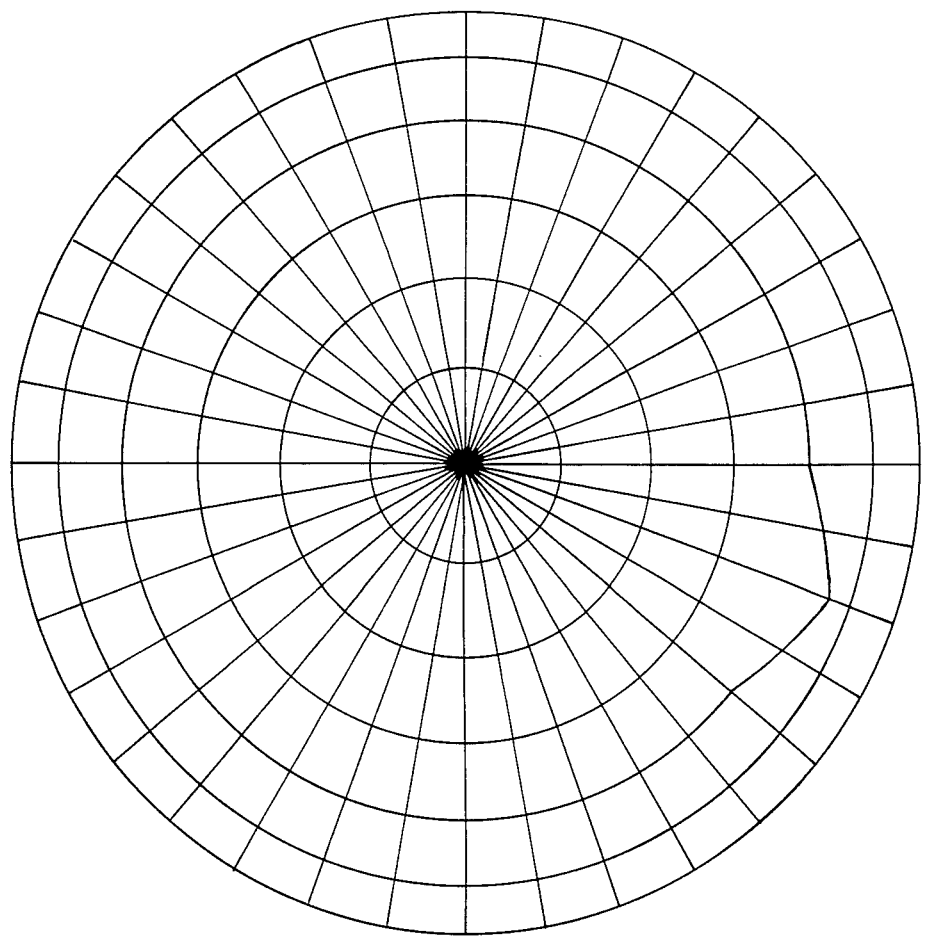
Figure 4C:
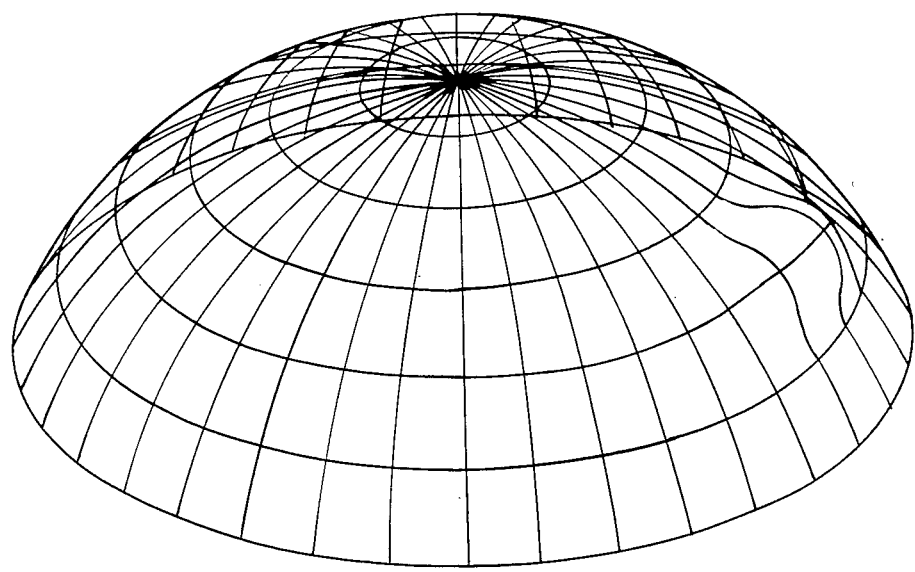

FIG. 4a illustrates a side view of the surface of the cornea. The deformation shown on the right-hand side represents an irregularity in the cornea surface. FIG. 4b shows a front view of the cornea. The irregularity of the cornea surface is shown by the deflection of the circle at the four o'clock position. FIG. 4c illustrates the perspective view of the cornea, the irregularity again being depicted on the right-hand side of the image.

I claim:

1. An apparatus for mapping the surface area of the cornea which comprises: probe means comprising a bundle of cylindrical pins reciprocally movable with respect to one another and having a forward end thereof adapted to measure the surface contour of a cornea, said bundle having a circular cross-section of at least 10 mm in diameter; means for locking said bundle of pins in a fixed position with respect to one another after said one end of the cylindrical pins is adapted to the shape of the cornea; detecting means for ascertaining the relative position of the ends of the pins to one another at the forward end of the bundle of pins; memory means for storing the relative position of each end of said pins; and graphing means for depicting the contour of the cornea on a surface based on the data stored in said memory means so as to permit observation by an operator.

2. A method of mapping the cornea which comprises:
(a) positioning a forward end of a probe containing a plurality of cylindrical pins projecting therefrom against the cornea of a patient so that each of said pins is in contact with the cornea;
(b) detecting the relative position of the bundle of pins with respect to one another;

(c) storing said relative positions in a memory means, said memory means having means to store data reflecting the relative position of each of said cylindrical pins; and (d) graphically depicting the contour formed by said one end of cylindrical pins based on the data stored in said memory means.

3. A probe useful in determining the contour of the cornea which comprises a plurality of cylindrical pins of equal length lying in the same longitudinal direction and forming a cylindrical bundle, the ends of said pins forming straight lines in the radial direction and a series of substantially annular rings, a sheathing enveloping the central portion of said pins so as to permit free longitudinal movement within said sheathing, and locking means adapted to prevent longitudinal movement of said cylindrical pins; said sheathing being such that the ends of the cylindrical pins project therefrom.

* * * * *